US008475642B2

(12) United States Patent
West et al.

(10) Patent No.: US 8,475,642 B2
(45) Date of Patent: Jul. 2, 2013

(54) SYSTEMS AND METHODS FOR MONITORING PLATING AND ETCHING BATHS

(75) Inventors: Alan C. West, Tenafly, NJ (US); Mark J. Willey, Portland, OR (US); Robert J. von Gutfeld, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 936 days.

(21) Appl. No.: 11/867,399

(22) Filed: Oct. 4, 2007

(65) Prior Publication Data
US 2008/0264801 A1    Oct. 30, 2008

Related U.S. Application Data

(63) Continuation of application No. PCT/US2006/012756, filed on Apr. 6, 2006.

(60) Provisional application No. 60/669,436, filed on Apr. 8, 2005, provisional application No. 60/759,377, filed on Jan. 17, 2006.

(51) Int. Cl.
*G01N 27/416* (2006.01)
*G01N 27/403* (2006.01)

(52) U.S. Cl.
USPC ............ 205/81; 205/775; 205/794; 204/434; 204/409; 204/400

(58) Field of Classification Search
USPC ................. 204/400, 409, 411, 434; 205/775, 205/794, 81
See application file for complete search history.

(56) References Cited

U.S. PATENT DOCUMENTS

| 3,582,478 A | 6/1971 | Kelly et al. |
| 4,169,770 A | 10/1979 | Cooke et al. |
| 4,217,183 A | 8/1980 | Melcher et al. |
| 4,229,264 A * | 10/1980 | Graunke .................... 205/789.5 |

(Continued)

FOREIGN PATENT DOCUMENTS

| CN | 1793434 | 6/2006 |
| JP | 60-204899 A | 10/1985 |

(Continued)

OTHER PUBLICATIONS

Darling et al, Micro Total Analysis Systems, '98, pp. 105-108, 1998.*

(Continued)

*Primary Examiner* — Alex Noguerola
(74) *Attorney, Agent, or Firm* — Baker Botts LLP

(57) ABSTRACT

Methods and systems for monitoring electrolyte bath fluids are provided. The electrolyte bath fluids can be electroplating, electroless plating or etching solutions. The monitoring systems employ microfluidic devices, which have built in microfluidic channels and microfabricated thin-film electrodes. The devices are configured with fluid pumps to control the movement and mixing of test fluids through the microfluidic channels. The microfabricated thin-film electrodes are configured so that the plating or etching bath fluid composition can be characterized by electrochemical measurements. The monitoring methods and system provide faster measurement times, generate minimal waste, and occupy dramatically reduced physical space compared to conventional bath-monitor systems. The monitoring systems and method also provide low-cost system and methods for measuring or monitoring electroless plating bath rates.

21 Claims, 10 Drawing Sheets

U.S. PATENT DOCUMENTS

| | | | |
|---|---|---|---|
| 4,283,259 A | 8/1981 | Melcher et al. | |
| 4,348,263 A | 9/1982 | Draper et al. | |
| 4,395,320 A | 7/1983 | Kasashima et al. | |
| 4,497,692 A | 2/1985 | Gelchinski et al. | |
| 4,629,539 A | 12/1986 | Imai | |
| 4,895,633 A | 1/1990 | Seto et al. | |
| 4,917,774 A * | 4/1990 | Fisher | 205/787 |
| 4,919,769 A | 4/1990 | Lin | |
| 5,202,291 A | 4/1993 | Charvat et al. | |
| 5,245,847 A | 9/1993 | Bando et al. | |
| 5,279,702 A | 1/1994 | Douglas | |
| 5,292,418 A | 3/1994 | Morita et al. | |
| 5,296,375 A | 3/1994 | Kricka et al. | |
| 5,364,510 A * | 11/1994 | Carpio | 134/2 |
| 5,378,343 A * | 1/1995 | Kounaves et al. | 204/413 |
| 5,704,493 A | 1/1998 | Fujikawa et al. | |
| 5,906,723 A | 5/1999 | Mathies et al. | |
| 5,928,880 A * | 7/1999 | Wilding et al. | 435/7.21 |
| 5,932,799 A | 8/1999 | Moles | |
| 6,042,712 A | 3/2000 | Mathieu | |
| 6,110,354 A | 8/2000 | Saban et al. | |
| 6,159,353 A | 12/2000 | West et al. | |
| 6,165,630 A | 12/2000 | Gehlhaar et al. | |
| 6,280,602 B1 * | 8/2001 | Robertson | 205/775 |
| 6,334,980 B1 * | 1/2002 | Hayes et al. | 422/68.1 |
| 6,391,559 B1 | 5/2002 | Brown et al. | |
| 6,423,207 B1 | 7/2002 | Heidari et al. | |
| 6,509,085 B1 | 1/2003 | Kennedy | |
| 6,521,118 B1 | 2/2003 | Starsvetsky et al. | |
| 6,532,642 B1 | 3/2003 | Wingo | |
| 6,936,167 B2 | 8/2005 | Hobbs et al. | |
| 7,079,760 B2 | 7/2006 | Hamelin et al. | |
| 7,192,559 B2 | 3/2007 | Chow et al. | |
| 2002/0046949 A1 | 4/2002 | Nakamura et al. | |
| 2002/0125142 A1 | 9/2002 | Sun et al. | |
| 2002/0195345 A1 | 12/2002 | Bentsen et al. | |
| 2003/0008473 A1 | 1/2003 | Sakaguchi et al. | |
| 2003/0029722 A1 * | 2/2003 | Erdosy et al. | 204/435 |
| 2004/0166504 A1 * | 8/2004 | Rossier et al. | 435/6 |
| 2005/0173253 A1 | 8/2005 | Huang | |
| 2005/0224359 A1 | 10/2005 | Su et al. | |
| 2005/0241948 A1 * | 11/2005 | Han et al. | 205/108 |
| 2006/0003579 A1 | 1/2006 | Sir | |
| 2008/0142367 A1 | 6/2008 | Von Gutfeld et al. | |
| 2008/0245674 A1 | 10/2008 | von Gutfeld et al. | |
| 2008/0264801 A1 | 10/2008 | West et al. | |
| 2008/0299780 A1 | 12/2008 | Elliott et al. | |
| 2009/0081386 A1 | 3/2009 | Von Gutfeld et al. | |
| 2010/0084286 A1 | 4/2010 | West | |
| 2011/0104396 A1 | 5/2011 | Von Gutfeld et al. | |

FOREIGN PATENT DOCUMENTS

| | | |
|---|---|---|
| JP | 04-066679 A | 3/1992 |
| JP | 2011071700 | 4/2011 |
| WO | WO9510040 | 4/1995 |
| WO | WO2006110437 | 10/2006 |

OTHER PUBLICATIONS

T. Kikuchi et al.; Local surface modification of aluminum by laser irradiation; Electrochimica Acta 47; 2001; pp. 225-234.

Lowenheim, F., Ed. John Wiley & Sons Inc.; Modern Electroplating; (3rd edition); 1974; pp. 591-625.

O.Mallory, Glenn; Hajdu, Juan B.; Fundamentals and Applications; American Electroplaters and Surface Finishers Society; 1990; pp. 193-204.

Ogden et al., "Cylic VOltammetric Stripping Analysis of Copper Plating Baths", pp. 229-240, Applications of Polarization Measurements in the Control of Metal Deposition, 1984; see entire document.

Ogden et al., "Cylic Voltaammetric Stripping Analysis of Copper Plating Baths", *Applications of Polarization Measurements in the Control of Metal Deposition*, 1984: 229-240.

Wills et al., "Laser micromachining of indium tin oxide films on polymer substrates by laser-induced delamination", *J. Phys. D: Appl. Phys.*, 42 (2009) 045306 (8pp).

U.S. Appl. No. 12/478,591, Jul. 9, 2012 Notice of Allowance.

U.S. Appl. No. 12/040,378, Jun. 28, 2012 Final Office Action.

U.S. Appl. No. 12/208,287, Jun. 29, 2012 Non-Final Office Action.

U.S. Appl. No. 11/767,461, Jul. 20, 2012 Amendment and Request for Continued Examination (RCE).

U.S. Appl. No. 11/767,461, Jul. 6, 2012 Advisory Action.

U.S. Appl. No. 11/767,461, Jun. 26, 2012 Response to Final Office Action.

U.S. Appl. No. 11/767,461, Feb. 11, 2013 Applicant Initiated Interview Summary.

U.S. Appl. No. 11/767,461, Feb. 7, 2013 Response to Final Office Action.

U.S. Appl. No. 12/040,378, Dec. 11, 2012 Non-Final Office Action.

U.S. Appl. No. 12/040,378, Nov. 27, 2012 Amendment and Request for Continued Examination (RCE).

U.S. Appl. No. 12/208,287, Dec. 28, 2012 Response to Non-Final Office Action.

U.S. Appl. No. 11/767,461, Oct. 3, 2012 Final Office Action.

* cited by examiner

SYSTEMS AND METHODS FOR MONITORING PLATING AND ETCHING BATHS

CROSS REFERENCE TO RELATED APPLICATIONS

This application is a continuation of International Application PCT/US06/012756, filed Apr. 6, 2006, which claims the benefit of U.S. provisional patent application No. 60/669,436 filed Apr. 8, 2005 and U.S. provisional patent application No. 60/759,377 filed Janury 17, 2006, each of which is incorporated by reference in its entirety herein.

BACKGROUND OF THE INVENTION

Electrolyte baths, which are used for electroplating and electroless plating of metals and alloys, typically contain a large number of chemical components. The concentration of many of these chemical components affects the plating rate and the properties of the plated materials. Furthermore, the plating bath composition changes over time due to, for example, chemical and electrochemical degradation of key bath components. Continuous or frequent monitoring of the electrolyte bath compositions is key to maintaining the bath components in proper proportion. The monitoring of the plating bath composition may be coupled with a control procedure that automatically or manually adjusts bath composition.

For convenience in description herein, the terms "plating," "electroplating" and "electroless plating," are used interchangeably with the equivalent terms "deposition," "electrodeposition" and "electroless deposition," respectively, as is common in the art. In addition to inorganic acids or salts, most commercial plating baths contain an extensive combination of organic additives that are present in very small concentrations. These organic additives (e.g., organic levelers, suppressors, inhibitors, accelerators, superfilling agents, surfactants, wetting agents, etc.) can have a dramatic effect on deposit properties and also influence the plating rate. Unfortunately, bath additive concentrations can change or age with time. This aging of concentrations requires that the bath used in a plating process should be continually or frequently monitored. Inorganic additives such as chloride ions also may be present in very small concentrations.

For electroplating processes, the concentration of organic additives in the plating bath may be the most difficult component to monitor and control. Furthermore, one or more additives are typically present at very low concentrations. In the case of copper plating processes, electrochemical methods, which indirectly measure the impact of the additives, are used for bath monitoring. To determine the concentration of individual additives, isolation methods have been developed for mixing plating bath samples with other fluids, which allow the influence of each additive to be isolated and measured individually. Implementation of these methods requires bulky equipment and produces significant amounts of waste per measurement. Furthermore, measurement times are unnecessarily long. For electroless plating processes, in addition to monitoring bath composition, other monitors are required for measuring plating rates.

Electrochemical measurement methodologies are commonly used for monitoring organic additives in electroplating baths. At least two methodologies based on cyclic voltammetric stripping (CVS) and pulsed cyclic galvanostatic analysis (PCGA) have had recent commercial success for monitoring copper electrodeposition processes in semiconductor manufacturing. (See e.g., commercial chemical monitoring systems sold by ECI Technology, Inc., 60 Gordon Drive, Totowa, N.J. 07512, and ATMI Inc., Danbury, Conn. 06810).

Successful application of electrochemical methods requires reproducible electrode surfaces and suitable electronics to allow for either two or three-electrode measurements in combination with an electrochemical cell. The suitable electronics typically may include a potentiostat, a galvanostat, or a power supply, which may further be connected to appropriate auxiliary equipment such as multimeters, voltmeters, coulometers, etc. A mechanism of recording the electrochemical measurements is also required. Typically this is achieved by interfacing a computer to the electronics. In a low-cost embodiment of the present invention, the recording device may be an analog readout of the measurements by the suitable electronics. Additionally, reproducible and controllable fluid flow within the electrochemical cell is required. A known fluid flow method exploits a rotating disk electrode for creating reproducible flow conditions. However, the disadvantage of a rotating disk electrode is the requirement of a relatively large volume of fluid in the electrochemical cell, generating significant waste since the fluid can generally not be re-used.

Since, in general, an electrochemical measurement is affected by all chemical constituents present, the electrochemical measurement is performed not only on the plating-bath sample but on combinations of the plating bath sample with one or more additional (second, third, etc.) fluids. For an acid-copper electrolyte the second fluid typically contains sulfuric acid and cupric sulfate at the same nominal concentration of the plating bath. The second fluid may also contain one or more of the previously mentioned plating additives. By repeating and recording the electrochemical measurement on a variety of combinations of the plating bath sample and different additional (e.g., second) fluids, methods have been created to determine the concentration of each additive in a bath. In conventional bath monitoring, the series of processes comprising combining fluids and repeating and recording electrochemical measurements not only generates excessive waste but is time consuming, requiring for a complete acid-copper bath at least one hour. Furthermore, because of the volume requirements of the various fluids, the plating bath monitor is large, occupying very valuable real estate in a fabrication facility.

Electrolyte baths are also used for electroetching or chemical etching of workpieces or parts. The etchants used may, for example, contain one or more chemical components or reactants. The rate of etching and quality of the surface of the part undergoing etching depends on the concentration of the etchant components present in the bath. An etchant after a period of usage in a bath will also contain additional chemical components, i.e., products formed by reaction of the reactants and the etched materials. These reaction products in some cases can lead to poisoning of the etchant bath. Furthermore, the original etching bath composition can change in time, for example, due to chemical and electrochemical degradation of key bath components. Therefore, it is desirable to monitor the etch bath composition with time, for example, in industrial manufacturing processes. In addition, it may be desirable to monitor a fresh etchant or electroplating bath as delivered from the manufacturer to obtain a reference level for certain constituents for future comparisons.

Methods of monitoring the etching baths are key to maintaining the bath components in proper proportion. The bath-monitoring method may be coupled with a control procedure that automatically or manually adjusts bath composition. The concentrations of one or more component may be monitored.

An individual monitored component may be an original etchant component or a reaction product that is formed during etching of a part. To determine concentration of individual components, which are typically present at very low concentrations, methods have been developed for mixing etching bath samples with other fluids, for example, to isolate the individual component from the influence of other components and for titration.

The etchant bath monitoring methodologies presently used require bulky equipment and produce significant waste per measurement, which makes them environmentally unfriendly. Furthermore, measurement times are long. In general, the monitoring determines the effectiveness of the etchant as constituents change with time during the etching process.

Consideration is now being given to improving systems and methods for monitoring and controlling plating bath and etching bath compositions.

SUMMARY OF THE INVENTION

The present invention provides systems and methods for monitoring the composition of electroplating and electroless-plating baths. The present invention also provides systems and methods for monitoring the composition of etchant baths.

The methods and systems for monitoring the composition of electroplating and electroless-plating employ miniaturized devices (e.g., a monitoring device or sampling probe) for collecting and measuring test or sample volumes of plating bath fluids. The devices, which may be fabricated on substrates or "chips," have microfluidic channels and reservoirs for collecting or isolating test or sample volumes of the bath fluids. The devices also have built-in thin film electrodes, which can be used for electrochemical measurements on the fluids collected or isolated in the microfluidic channels and reservoirs. The microfluidic channels and reservoirs, and the thin film electrodes, may be constructed in suitable geometrical configurations on chips or substrates using common microfabrication techniques. Conventional pumps or other techniques may be used to control the movement and "on-chip" or "off-chip" mixing of test fluids and chemical reagents through the microfluidic channels and reservoirs.

The methods and systems for monitoring etching bath composition, like the methods and systems for monitoring the composition of electroplating and electroless-plating, use devices based on microfluidic channels and microfabricated thin-film electrodes, controlled movement and mixing of fluids, and electrochemical methods of characterizing the bath.

In one embodiment for monitoring etchant constituents, a well-characterized electrolyte is used to first cause a deposition onto an inert electrode within a microchannel for a pre-determined time. Subsequently, the etchant is introduced over the same electrode to cause electrochemical stripping of the just deposited metal and a measurement of the stripping charge is used to determine the effectiveness of the etchant. In another embodiment, the etchant is introduced into a microchannel and monitored, after which a second fluid is mixed with the original etchant and monitored to determine the effectiveness of the etchant. The effectiveness of the etchant is determined from a comparison of the monitoring curves based on known monitoring standards for the etchant and the mixed etchant/second fluid.

The invention advantageously provides a dramatic reduction in the size of an etchant bath-monitor system, not only because of the reduction in the size of the monitor device, but because of very significant reduction in the size of reservoirs that contain fluids used for mixing with the etchant bath sample. Similarly, the invention advantageously provides monitoring systems, which are substantially smaller compared to prior art bath-monitor systems that are commonly used in the industry for electroplating and electroless plating operations. The reduction in monitoring system size comes about not only because of the miniaturization of the monitoring device or sampling probe, but also because of a very significant reduction in the size of reservoirs that contain fluids used for mixing with a plating-bath sample. Further, the monitoring systems of the present invention generate significantly smaller amounts of waste per measurement and reduce the time of measurement.

The monitoring systems also may facilitate low-cost methods or procedures for monitoring electroless plating rates. In a rate measurement procedure, an electroless bath fluid sample flows through the microchannels in a sampling probe to deposit a metal or alloy on an electrode for a fixed period of time. Next, a second fluid in the form of a stripping electrolyte or reagent flows over the electrode, which is now polarized or charged anodically, to strip the just deposited metal or alloy. A measurement of the total stripping charge leads to a determination of the electroless plating rate.

BRIEF DESCRIPTION OF THE FIGURES

Further features of the invention, its nature, and various advantages will be more apparent from the following detailed description of the preferred embodiments and the accompanying drawings, wherein like reference characters represent like elements throughout, and in which:

FIG. 3 shows the overpotential change due to the change from a solution of 0 mg/l PEG and SPS to one containing 300 mg/l PEG and 5 mg/liter SPS.

FIG. 4 shows the change in potential due to the change from a solution containing 300 mg/l PEG and 5 mg/l SPS to one containing only 300 mg/l PEG but no SPS.

DETAILED DESCRIPTION OF THE INVENTION

Figure 1:
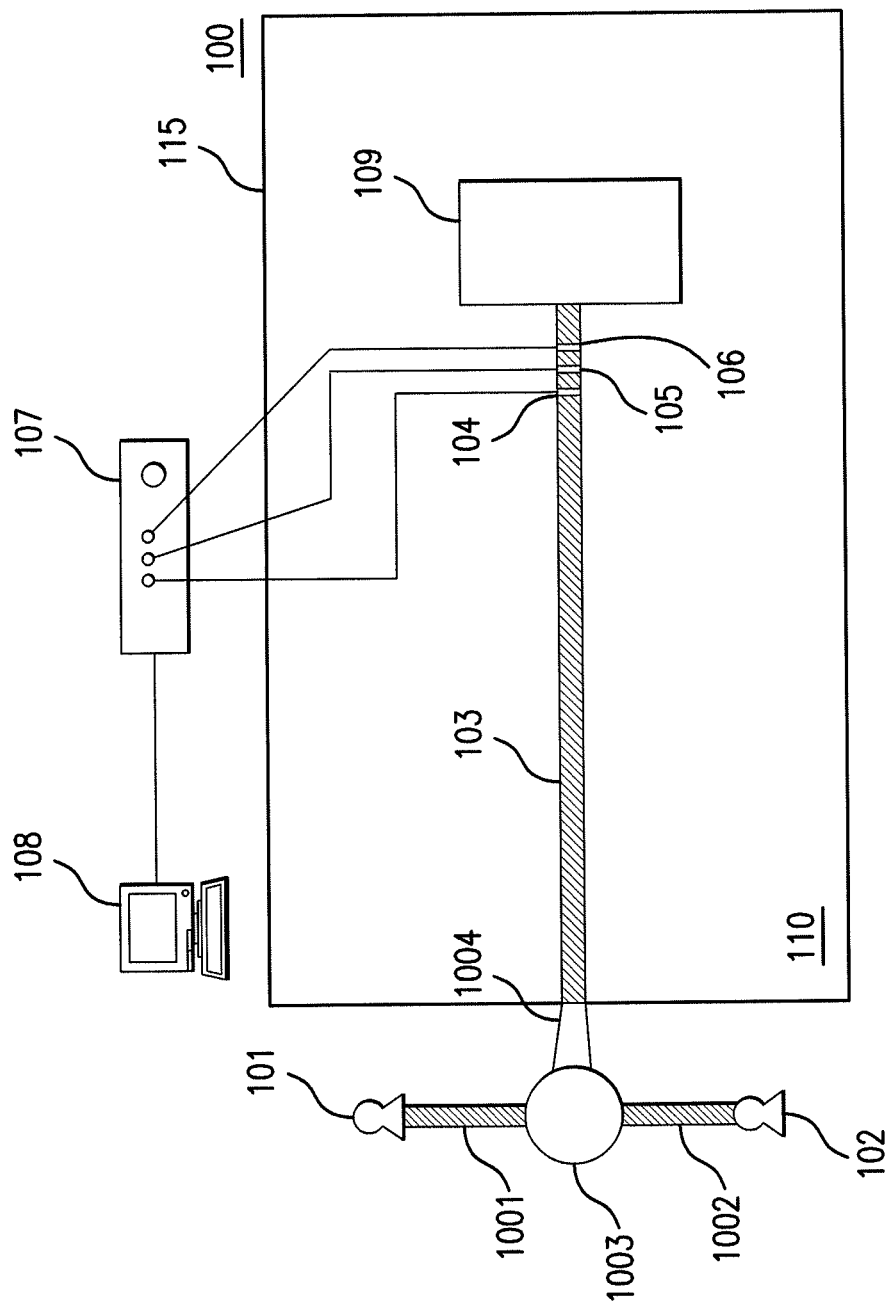
FIG. 1 is a schematic illustration of a bath monitoring system using a micro-fluidic channel and off-chip mixing, in accordance with the principles of the present invention.

Systems and methods are provided for monitoring electrolyte baths used in electroplating and electroless plating processes. These monitoring systems and methods employ miniaturized sampling probes or devices to collect and measure the properties of bath fluid samples. The inventive systems and methods are further adapted for monitoring electrolyte baths used in etching processes.

In one mode of operation useful for monitoring electroplating and electroless plating processes, the systems and methods of the present invention can be used to monitor concentrations of the multiple organic and/or inorganic plating bath additives that are used in plating processes. In another mode of operation, the monitoring systems and methods can be used to measure in almost real time the electroless plating rate obtained from a given electrolyte bath composition.

The concentration and/or rate information generated by the monitoring systems and methods may be utilized by plating bath operators to advantageously schedule replenishment of additives or other replacement of bath fluids at critical times, for example, prior to introducing a valuable workpiece into a plating bath.

The monitoring systems and methods can have a significant impact on the results and economics of common industrial plating processes. One such exemplary process of current industrial importance relates to semiconductor device or chip manufacturing. Electroplating is used to deposit copper onto semiconductor wafers during the fabrication of electronic devices or chips. The economics of chip manufacturing requires a very high yield for each individual processing step, which can be greatly improved by maintaining electrolyte bath composition within a prescribed window of operation. Thus there is a significant demand for plating-rate monitors. Presently available plating-rate monitors used in semiconductor chip fabrication facilities are spatially large, require a significant amount of time to perform a complete bath analysis, and generate significant waste product for every measurement. The present invention enables a dramatic reduction in system size, reduces waste volumes by up to a factor of 1000, and also reduces analysis and measurement time by as much as a factor of 5 to 10.

These dramatic improvements are made possible by utilizing microfluidics, an interdisciplinary area of science and technology in which microfabrication methods are used to create small structures, such as channels through which fluids can be pumped at extremely low volumetric flow rates. The fluid pumping mechanisms can be either "on-chip" as an integral part of a microfabricated device or probe, or may be provided as an "off-chip" part of the monitoring system.

The present invention is advantageously implemented by combining microfluidic technologies with electrochemical measurement techniques. Flow structures and methods for creating and controlling flows are combined with chemical or physical methods, to create powerful and versatile sensors.

While the advantages of the present invention may be readily understood or described with reference to the aforementioned copper electrodeposition processes and electrochemical monitoring methodologies, it will be understood that the present invention can be utilized with other electrochemical methods or materials and is not limited to examples that are used herein only for purposes of illustration.

The systems and methods of the present invention advantageously utilize microfluidic technologies to provide a very reproducible and controllable fluid flow near the electrode surfaces while maintaining the liquid volumes used to a minimal amount.

FIG. 1 shows an exemplary plating bath monitoring system 100 based on microfluidics. System 100 includes an exemplary sampling probe 110 having a microchannel 103 fabricated on a substrate or chip. Microchannel 103 may have a length l, a height h and a width w. A set of closely spaced electrodes 104-106 may be disposed on the interior surface of microchannel 103 perpendicular to its length. The set of electrodes includes a working electrode 105, which is the primary electrode used to monitor the test solution in microchannel 103, a counter electrode 106 that is necessary for electric current to flow through the electrolyte, and an optional reference electrode 104 that can be used in three-electrode measurements to allow for easier interpretation of processes occurring at the working electrode 105.

Electrodes 104, 105, and 106 may be fabricated from any suitable materials. For example, working electrode 105 and counter electrode 106 may be made of platinum (Pt), which is known to be an ideal electrode material due to its stability in many electroplating baths. In the case of an acid-copper plating bath monitoring system, reference electrode 104 may be fabricated as a thin film of Pt upon which a second thin film of copper is deposited. Other materials may be more suitable or appropriate for monitoring baths other than copper plating baths. It will be understood that the present invention is not limited to the use of Pt as an electrode or part of an electrode structure.

Similarly, the substrate or chip from which probe 110 is fabricated may be any suitable materials. The suitable materials may, for example, be selected with consideration to the plating bath chemistries and/or available microfabrication techniques. (See e.g., Marc J. Madou, Fundamentals of Microfabrication: The Science of Miniaturization, $2^{nd}$ Ed., CRC Press, New York (2002)). An exemplary probe 100 has been fabricated using an oxidized silicon (Si) wafer 115 on which microchannel 103 was formed in a polydimethylsiloxane (PDMS) over layer. Microchannel 103 was fabricated in polydimethylsiloxane (PDMS) using known microfabrication methods. The PDMS layer containing the microchannel 103 is easily assembled on top of the Si wafer 115 on which a set of electrodes 104, 105, and 106 was preformed. For the fabrication of the electrodes, a thin adhesion layer including Ti, Al, and/or Cr was first deposited onto a lithographically pre-patterned oxidized Si surface. Then on top of the adhesion layer, Pt was deposited via electron beam vapor deposition. Electrodes 104, 105, and 106 were disposed on the Si wafer surface, which made up the bottom of the microchannel 103. The electrodes could alternatively be disposed on either the side or top of microchannel 103.

In the operation of system 100, test volumes of fluid 1001 and fluid 1002 corresponding to a plating bath sample and a second fluid are mixed off probe 110 using pump 101 and pump 102. The mixed test volume or solution 1004 is inserted into microchannel 103 through a manifold 1003 which is connected between pumps 101 and 102 and microchannel 103. Once test solution 1004 has filled the microchannel 103, suitable electronics such as potentiostat 107 are used for electrochemical measurements that characterize the properties of test solution 1004, while the fluid flows continuously through microchannel 103. After passage through microchannel 103, test solution 1004 is expelled as waste into a fluid disposal chamber 109. After the first electrochemical measurement is completed and results are recorded through the use of computer 108, the same test solution 1004 may be generated if desired, for example, for a confirmation measurement, by again mixing additional fluid samples 1001 and 1002 in manifold 1003.

Test solutions 1004 having different chemistries may be prepared by mixing different types of fluid 1002 with fluid 1001 in manifold 1003. The different chemistries may be selected as suitable, for example, for measuring specific additives in the plating bath. In a plating bath characterization procedure, the same or a number of different test solutions 1004 may be measured one or more times to characterize the plating bath components in as much detail as desired. It may be necessary or desirable to clean, condition, or calibrate electrodes 104-106 and/or microchannel 103 periodically during the characterization procedure, or before or after particular test solution measurements. For this purpose, suitable cleaning, conditioning, or calibration fluids may be inserted in microchannel 103 at convenient times via mixing manifold 1003. The cleaning, conditioning, or calibration processes may be electrochemical processes that involve passing current through the electrodes 104-106.

Microchannel 103 can also be fabricated from glass, polymethyl methacralate (PMMA) or the like. Furthermore, the channels can be heated to any desired temperature above room temperature, consistent with the melting temperature of the channels by surrounding the microfluidic device on at least one side with heating elements connected to a feedback temperature controller (not shown). This enables the etchant or any electrolyte to be measured at some desired fixed temperature using the microfluidic device. Other means of heating, such as the use of indium tin oxide coatings on the channels to carry current for Joule heating of the channel, or thermoelectric devices in contact with the channel, also may be used when desired.

Figure 2:
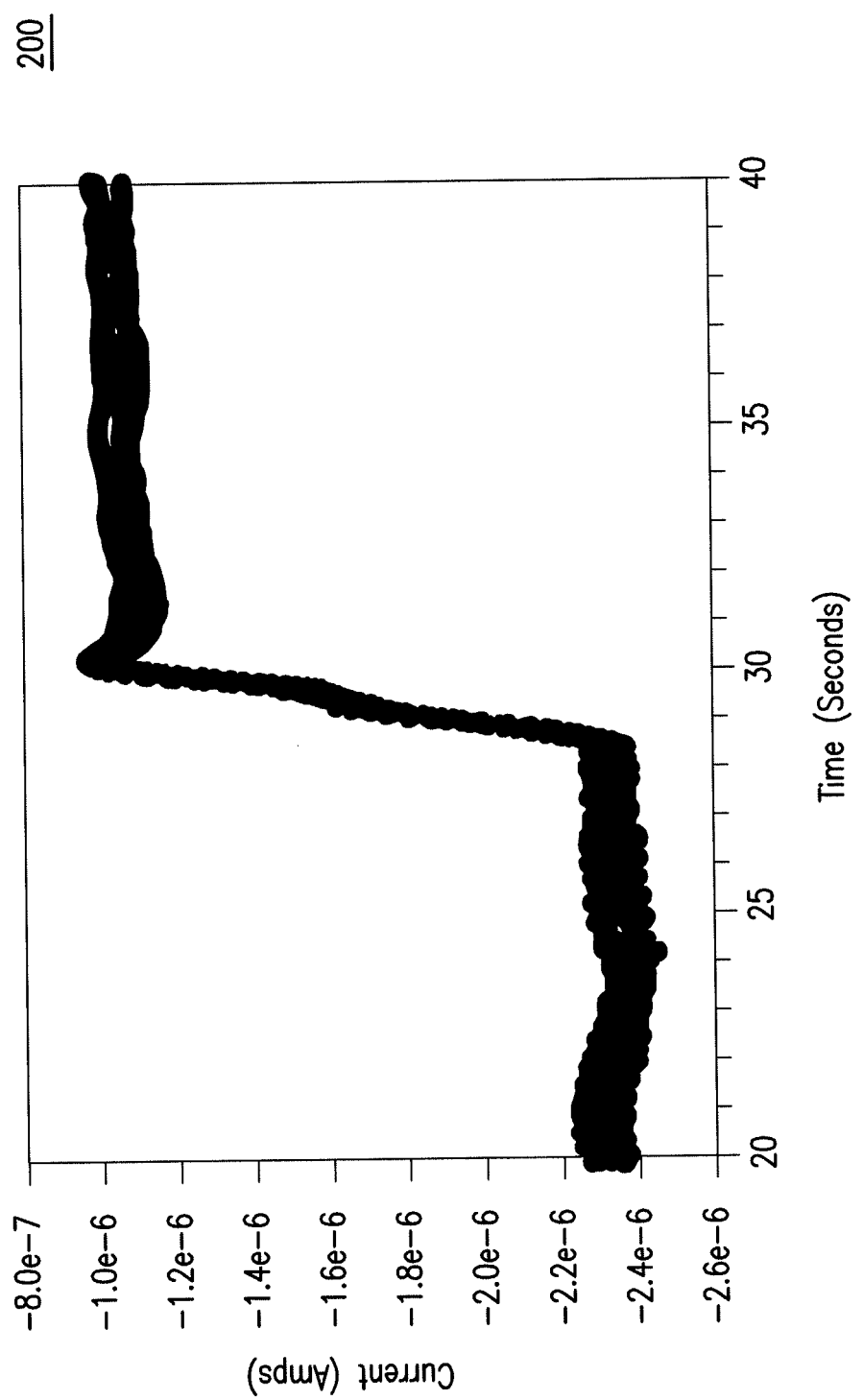
FIG. 2 is a graph obtained using the bath monitoring system of FIG. 1, in accordance with the principles of the present invention. The graph shows a step change in current resulting from a step change in concentration of tri-iodide ions.

An experiment was conducted using system 100 to measure electrochemical response sensitivity. FIG. 2 shows the electrochemical response measured by computer 108 using potentiostat or power supply 107, which was electrically connected to electrodes 104, 105 and 106. In the experiment, working electrode 105 was held at a preset potential after insertion of an aqueous test solution 1001 containing 0.1 M KI, 0.001 M $I_2$, immediately followed by a second test solution 1004, which is composed of 50 volume percent of a first fluid 1001 containing 0.1 M KI and 0.001 M $I_2$ and a second fluid 1002, which contained 0.1 M KI but no $I_2$. It may be noted that during the experiment, fluid 1001 underwent no mixing during the first insertion into the microchannel 103, and then was mixed in the manifold 1003 with fluid 1002 to obtain mixture 1004. In this case, the electrochemical response shown is the measured and recorded current flowing through the working electrode 105 resulting from a potentiostatic experiment in which the working electrode potential was maintained at a certain value to ensure that the electrode reaction rate was controlled by mass transfer of iodine to the electrode surface. Series of such experiments have been conducted to characterize the fluid flow and mass transfer within microchannel 103. Based on a series of experiments of the type shown in FIG. 2, we have found that the electrochemical response reaches a steady value after an exchange of fluids of less than one second. Furthermore, the values of the two steady state currents from time t<28 seconds and t>~30 s, respectively, in FIG. 2 are found to be consistent with that predicted by a theoretical analysis using the steady state convective diffusion equation.

For the experimental results shown in FIG. 2, each thin-film electrode 104, 105 and 106 had a thickness of 30 nanometers, deposited on a 5 nanometer chrome adhesion layer, giving a total electrode height of approximately 35 μm. The width of each electrode was 86 micrometers, and the spacing between consecutive electrodes was 100 micrometers. The microchannel areal dimensions may be typically less than 1 mm across. For the case of the experimental sample probe 110, the microchannel dimensions were 65 micrometers (height) and 533 micrometers (width). A volumetric flow of 10 ml/hour was used to obtain these results. Similar experiments were performed using volumetric flow rates between 1 and 20 ml/hour. In order to minimize waste volume generated by system 100, the volumetric flow rate through microchannel 103 can be even further reduced. It should be noted that the waste volume is typically equal to the total fluid pumped through microchannel 103 into fluid disposal chamber 109. By decreasing the dimensions of microchannel 103 to a width of approximately 10-50 micrometers, the flow rate can be further reduced by a factor of 10 to 50 resulting in a flow rate of less than 1 ml/hr. This reduces the waste produced by system 100 proportionally by a factor of 10 to 50.

Figure 3:
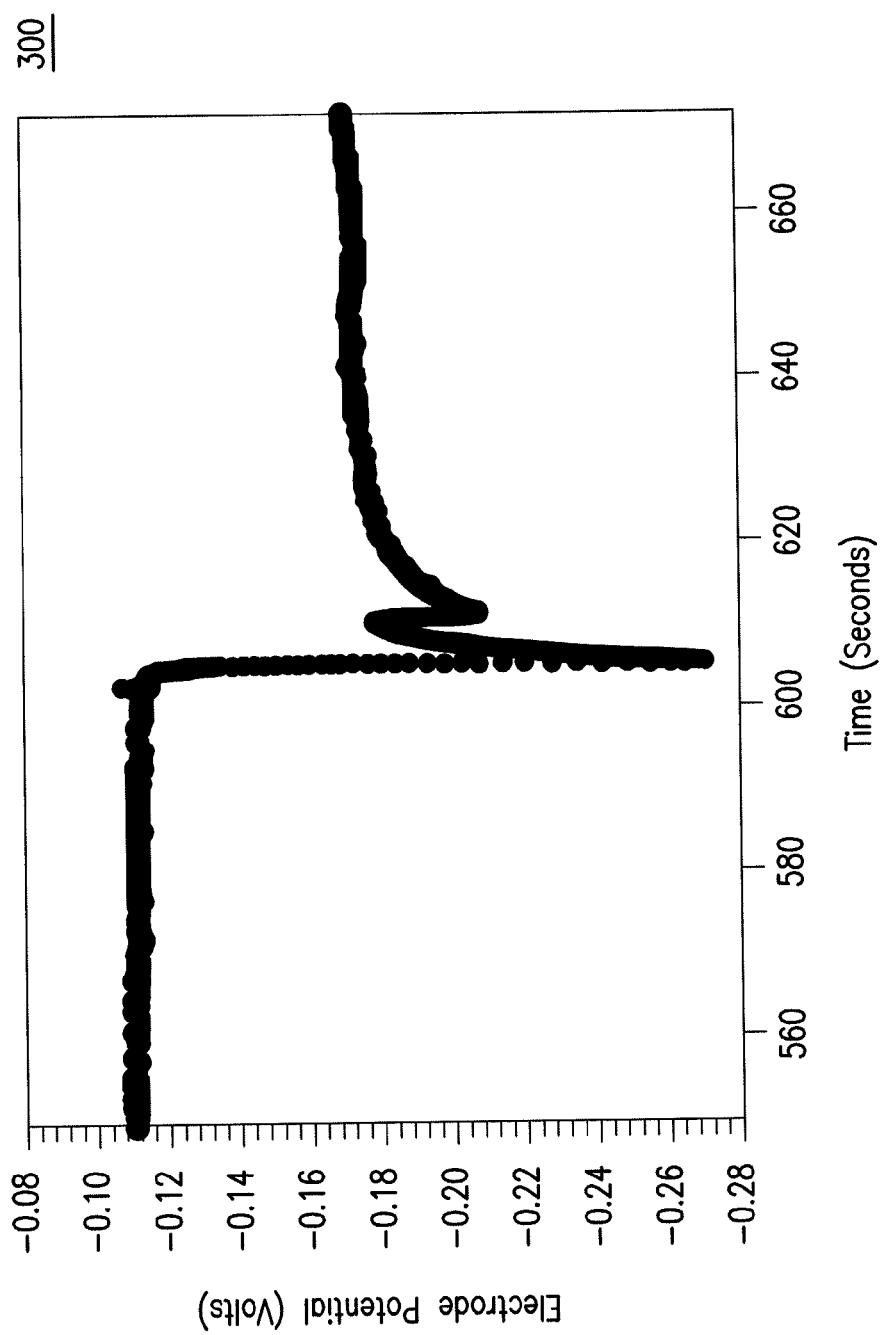
FIG. 3 is a graph illustrating the change in overpotential obtained using the bath monitoring system of FIG. 1, in accordance with the principles of the present invention.
Figure 4:
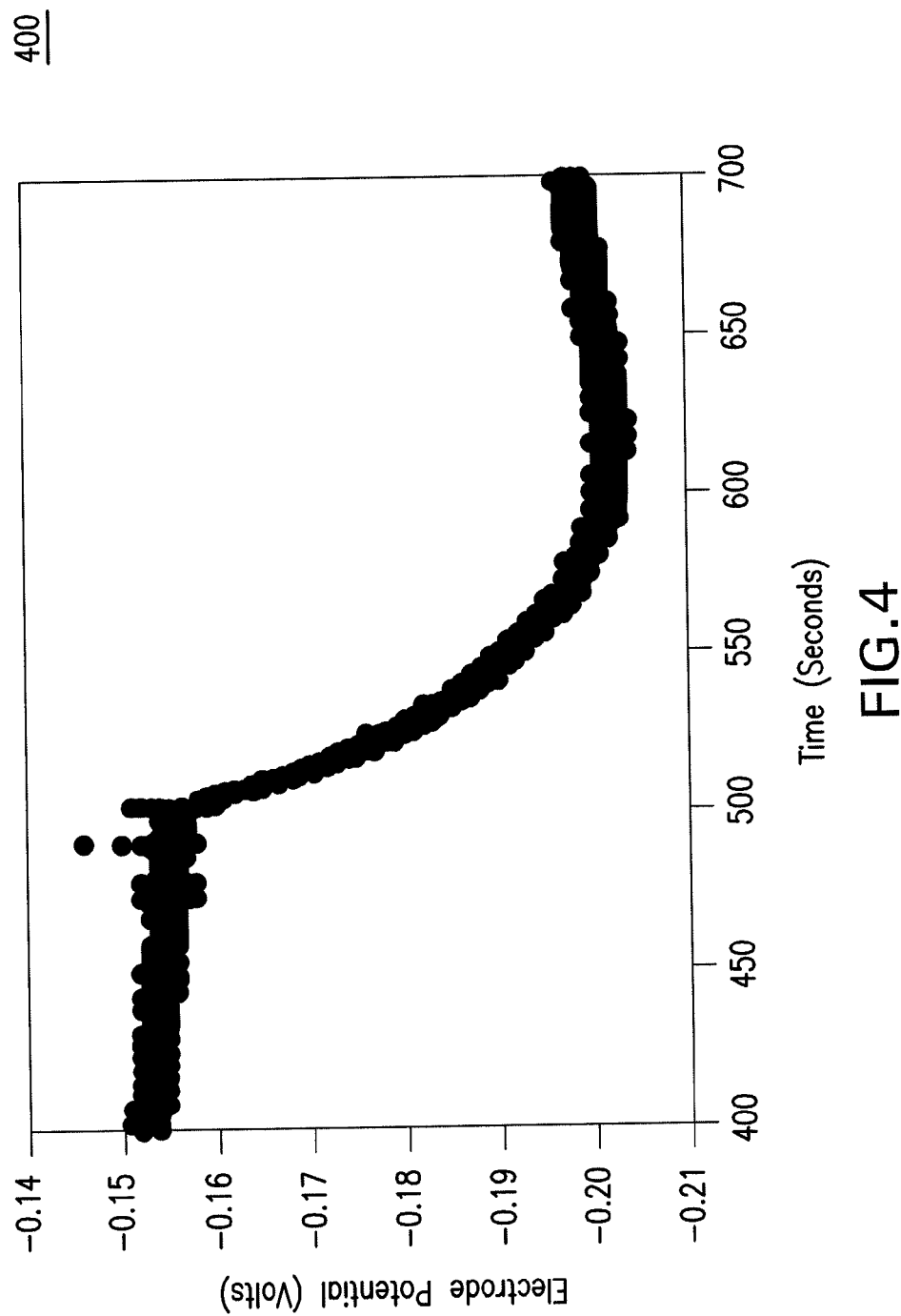
FIG. 4 is another graph illustrating the change in overpotential obtained using the bath monitoring system of FIG. 1, in accordance with the principles of the present invention.

FIGS. 3 and 4 show the behavior of the inventive microfluidic device or probe when utilized to study an acid-copper plating bath containing 0.24 M cupric-sulfate, 50 mg/liter of chloride ions, and 1.8 M sulfuric acid. In both Figures, the electrochemical results are shown as graphs of the working electrode 105 potential relative to reference electrode 104 versus time. These results were obtained using a galvanostatic mode of operation with an applied current of $2.5 \times 10^{-6}$ amperes. In all cases, the potential was recorded with computer 108. Furthermore, the flow rate was 10 ml/hour, areal dimensions of microchannel 103 were 65 micrometers in height and 533 micrometers wide, and the working electrode 105 width was 86 micrometers. The spacing between consecutive electrodes 104, 105 and 106 was less than 0.5 mm and is 100 micrometers for the particular system 100 shown in FIG. 1. In this case electrodes 104, 105 and 106 were comprised of a 70 nanometer thick film of Pt deposited onto a 10 nm thick Ti adhesion layer, giving an electrode height of approximately 80 nm.

FIG. 3 shows an abrupt change in potential when the deposition solution is switched from one containing 50 mg/liter chloride to one containing the same amount of chloride ions, 300 mg/liter of polyethylene glycol (PEG), with a molecular weight of 3350 g/mol, and 5 mg/liter bis sulfopropyl sulfonate (SPS). Note the abrupt change in potential at approximately 600 seconds, which demonstrates the inhibition of deposition due to the presence of PEG. FIG. 4 shows a step change in potential due to a step change in concentration from a plating bath solution containing 300 mg/liter of PEG and 5 mg/liter SPS to one containing only 300 mg/liter of PEG. Notice, as in the FIG. 3, that the inhibition is increased at a time of approximately 500 seconds, which is the approximate time at which the PEG solution enters the system. FIGS. 3 and 4 show the ability to electrochemically monitor bath composition through the change in potential during galvanostatic control.

Alternatively or additionally, dynamic experiments, in which either the electrode potential or current is varied as a function of time and the resulting variation in current or potential is measured, may be used to characterize bath composition.

Experiments were also successfully conducted in a range of flow rates from 1-20 ml/hour. Significantly lower flow rates are made practical by reducing the areal dimensions of microchannel 103. For example, a microchannel with areal dimensions of 20 micrometers wide and 23 micrometers in height has a cross-sectional area that is roughly 100 times smaller than microchannel 103 used to obtain results in FIGS. 3 and 4. With this reduction in cross-sectional area, a volumetric flow rate between 0.01 and 0.2 ml/hour permits similar microfluidic device performance.

The results shown in FIGS. 3 and 4 for the two distinct test solutions demonstrate that the monitor is responsive to changes in additive composition and that the response time is rapid. Such electrochemical measurements are correlated with bath composition to establish the preferred bath monitoring methodology. While the electrochemical measurements shown in FIGS. 2, 3 and 4 are based on potentiostatic and galvanostatic modes of operation respectively, other electrochemical measurements such as CVS and PCGA often provide greater sensitivity to changes in bath composition and may be preferred for use with the present invention.

Figure 5:
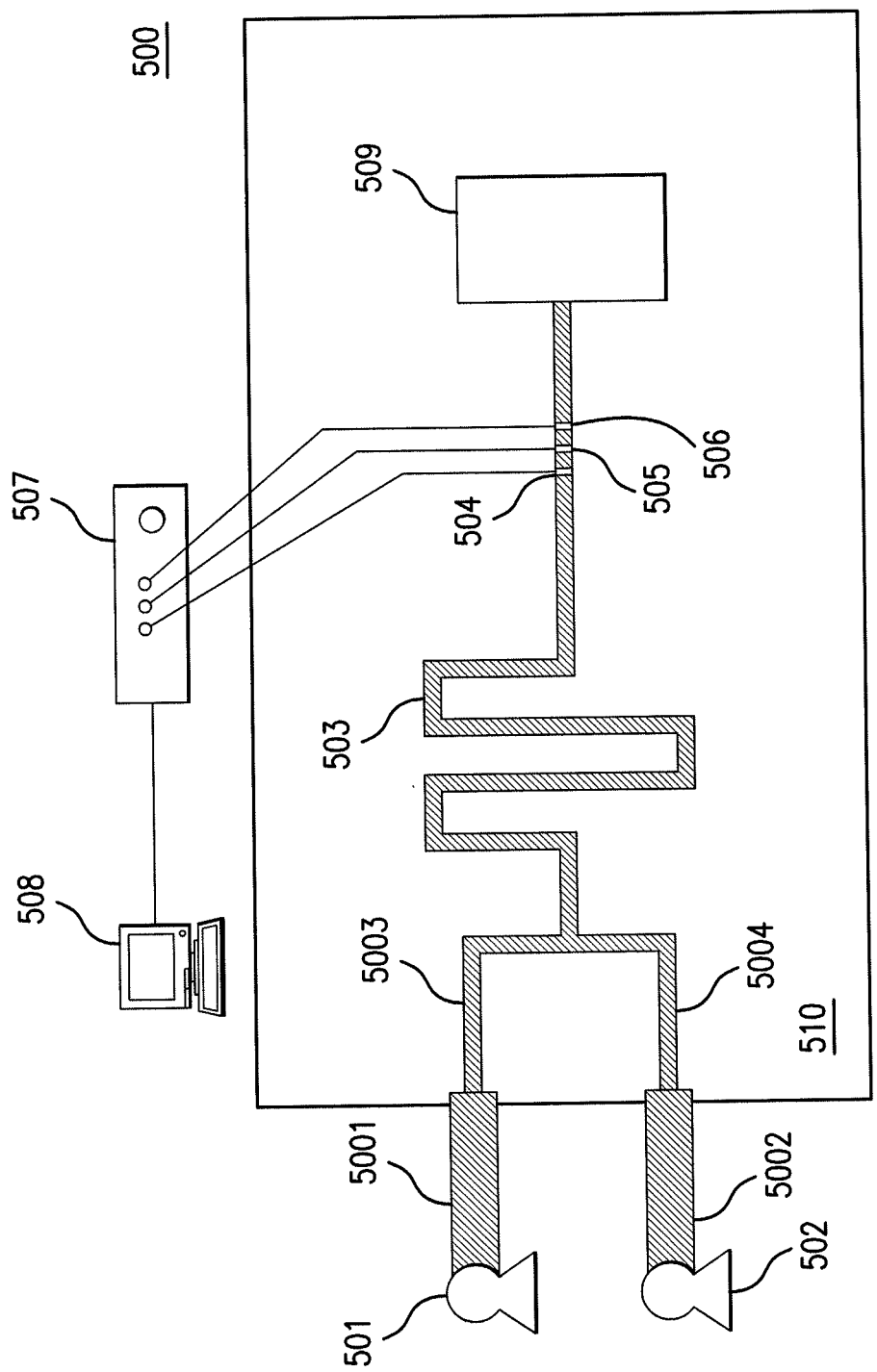
FIG. 5 is a schematic illustration of a microfluidic device or probe for measuring plating or etching electrolyte bath composition using on-chip mixing of two solutions, in accordance with the principles of the present invention.

FIG. 5 shows an exemplary system 500 in which the mixing of a fluid 5001 and a fluid 5002 occurs on substrate 510 into which these fluids are injected through pumps 501 and 502 respectively. Potentiostat 507, computer 508, and fluid disposal 509 provide functions similar to those described with reference to similar elements for the system 100 of FIG. 1. In the operation of system 500, test fluids are injected into port 5003 and port 5004. The two fluids flow through separate microchannels 5003 and 5004 and combine at a junction point after which they flow together into microchannel 503. It is important that the two fluids are well mixed prior to reaching reference electrode 504, working electrode 505 and counter electrode 506. Depending on the fluid flow conditions, molecular diffusion may be the primary mode of mixing. For sample probes such as depicted in FIG. 5, the length of microchannel 503 may need to be relatively long to allow for adequate mixing. A simple formula can be utilized to estimate the required length of microchannel 503, $L_{channel}$, to ensure mixing:

$$L_{channel} > \frac{w_{diff}^2 v_{avg}}{D}, \quad (1)$$

where $w_{diff}$ is the diffusion distance and is typically a value between microchannel 503 width w and microchannel 503 half-width, depending on the ratio of volumetric flow rates of fluid 5001 and fluid 5002. The variable $v_{avg}$ is the average fluid velocity in microchannel 503, and D is the diffusion coefficient of a representative species. The average fluid velocity in microchannel 503 can be related to the volumetric flow rate Q through the following equation:

$$v_{avg} = \frac{Q}{hw}, \quad (2)$$

where h is the height of microchannel 503. To ensure that the channel length is not excessively long, a channel width w typically less than 100 micrometers may be required for this embodiment of the invention.

Alternatively, on-device mixing schemes to decrease mixing times below those required by molecular diffusion can be adopted. For example, one fluid inlet channel, through which a first fluid flows, may be split into two separate channels, and the two separate channels subsequently joined to a third microchannel, through which a second fluid flows. By sandwiching the second fluid between two streams of first fluid, the effective diffusion distance can be decreased.

Figure 6:
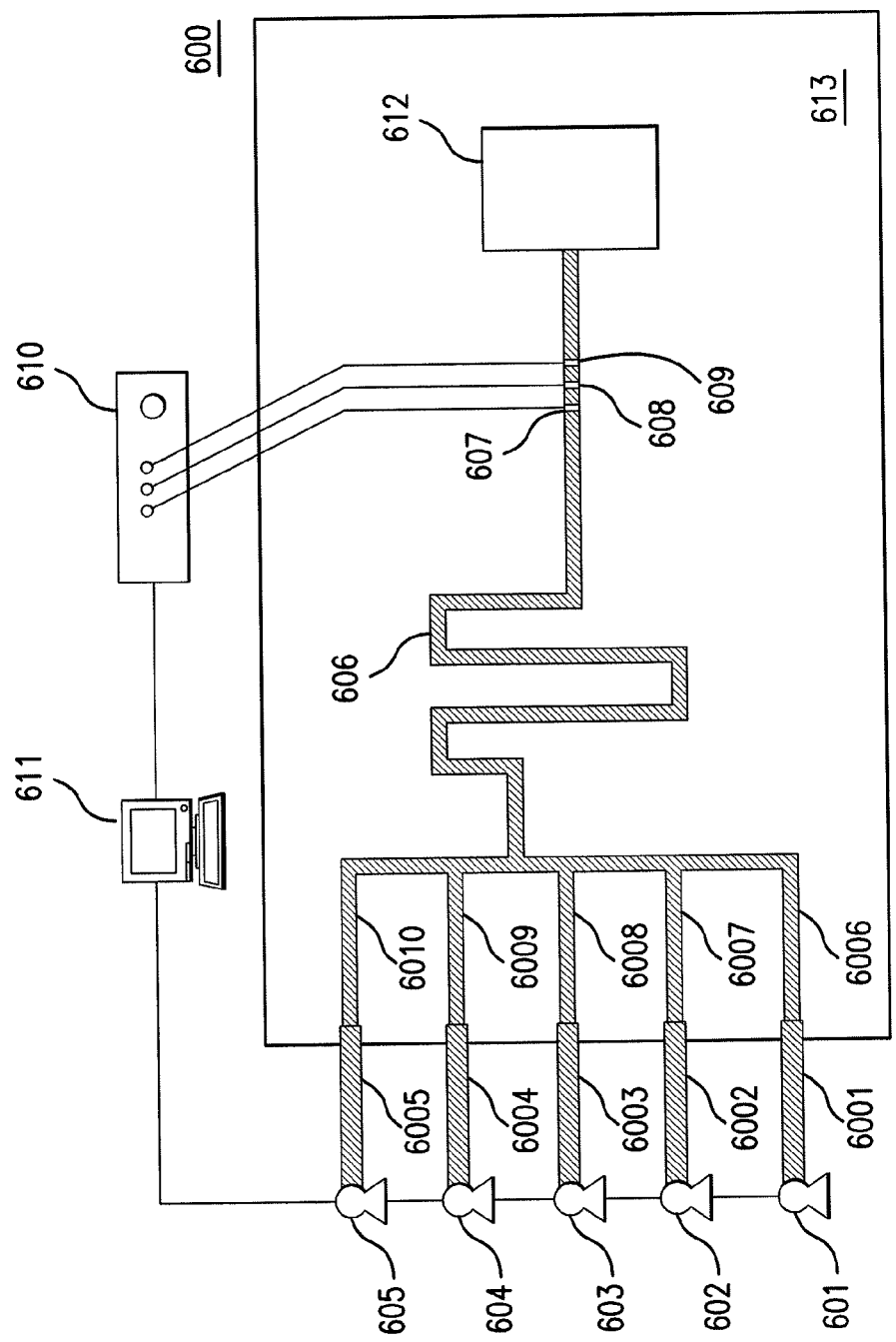
FIG. 6 is a schematic illustration of another microfluidic sampling device or probe for measuring the bath composition of a mixed solution. The probe has n inlets for mixing fluids located on-chip, which can be used to prepare the mixed solution for measurement in accordance with the principles of the present invention.

System 500 as shown in FIG. 5 has two exemplary inlet ports 5003 and 5004. With such an inlet configuration, it may be possible to sequentially measure the electrochemical response of two or more fluids by switching fluids 5001 and 5002 that are inserted into port 5003 and port 5004. A sampling device may include more than two inlet ports. FIG. 6 shows, for example, system 600 based on sample probe/substrate 613 having five ports 6006, 6007, 6008, 6009 and 6010 that are fed by pumps 601, 602, 603, 604 and 605, respectively. It will be clear to those skilled in the art that any number of additional pumps and inlet ports can be added. In the operation of system 600, fluids 6001, 6002, 6003, 6004 and 6005 are connected to the respective ports, and their flow rates may be externally controlled by computer 611. This version of the sampling probe permits the admixture of two or more fluids to produce the test solution. Any number of combinations of the fluids 6001, 6002, 6003, 6004 and 6005 can be used as a test solution.

FIG. 6 also shows a potentiostat 610, which is used to control reference electrode 607, a working electrode 608, and a counter electrode 609. Port 612 may be a disposal port similar to port 109 shown in FIG. 1. The pumps in system 600 are electrically connected to computer 611, which allows for automated control of the mixing. In a similar fashion, pumps 101, 102, 501, and 502 may be configured to control the fluid flow speed by way of computers 107 and 507 that are shown FIGS. 1 and 5 using techniques known in the art.

For the example systems shown in FIGS. 1, 5, and 6, the reference electrodes 104, 504 and 607 are present in the same microchannel as the working electrodes 105, 505 and 608 and counter electrodes 106, 506 and 609, all of which are electrically connected to potentiostat or power supplies 507, 107 and 610. Since these reference electrodes are in contact with the test solution or fluid, their response may not be as reproducible as desired for certain applications. For these applications, a modified system 700 shown in FIG. 7 may be more suitable. Mixing of inlet fluids can be done in system 700 through the on-substrate mixing of system 500 or the off-substrate mixing of system 100. While the preferred embodiment of pumps 701, 702, and 703 are attached to the substrate 713 it is clear that one could choose to have one or more pumps on substrate 713 as well. The reference electrode 709 may be placed in a separate microchannel 705, connected via a microchannel bridge 706 to microchannel 704. Microchannel 704 contains the working electrode 707 and counter electrode 708. In the operation of system 700, pumps 701, 702, inject fluids 7001 and 7002 into inlet ports 7004 and 7005, respectively. Both inlet ports subsequently merge with microchannel 704. Pump 703 injects reference fluid 7003 into microchannel 705. Potentiostat 710, computer 711 and fluid disposal 712 function as previously described with reference to FIGS. 1 and 5. Also, pumps 701, 702, and 703 can control the fluid flow speed by utilizing computer 711 using techniques known in the art.

Figure 7:
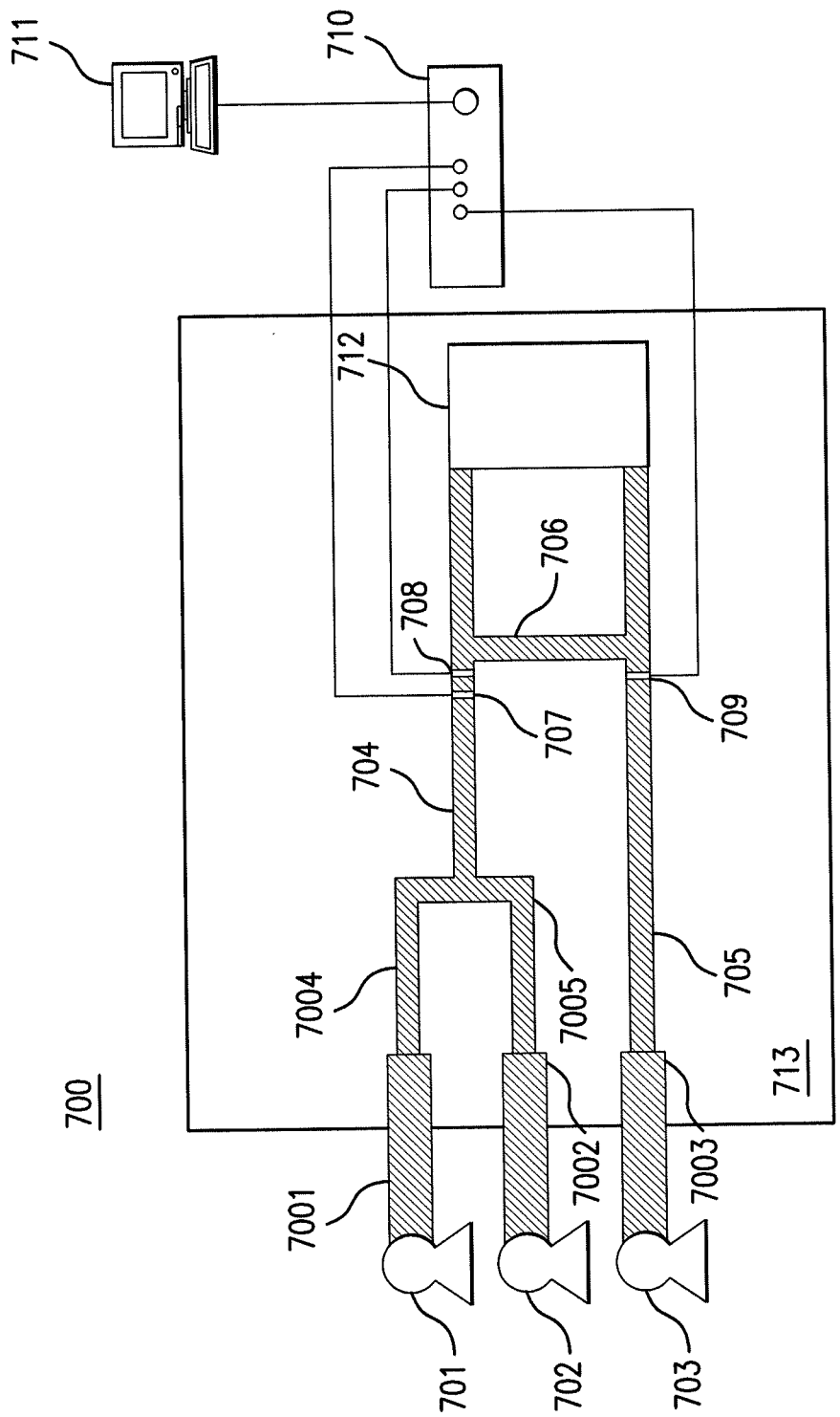
FIG. 7 is a schematic illustration of another microfluidic sampling device or probe for measuring the bath composition, in accordance with the principles of the present invention. The probe has two separate flow channels, one of which is used with the working and counter electrodes and the second of which is used with the reference electrode.

In general, for certain measurements, it may be preferred to have an array of microchannels including at least one pair of closely spaced microchannels where the microchannels forming the pair are connected downstream from placement of at least one of the electrodes. To utilize a three electrode measurement, the fluid in the microchannel containing a working electrode must be in contact with the fluid in the microchannel containing a reference electrode. Referring to FIG. 7, contact of the fluids in microchannels 704 and 705 through microchannel bridge 706 could result in mixing of the fluids. Any extent of mixing would occur downstream from the working and reference electrodes and therefore this mixing is unlikely to affect the measurement by potentiostat 710, and computer 711. Element 712 indicates a fluid disposal chamber for system 700.

In selecting a reference electrode and reference fluid, reproducibility is a primary concern. For the case of acid-copper bath monitoring, the reference electrode may be a thin film of Cu deposited onto a Pt thin film, and the reference solution could be an acid-copper bath, which may or may not contain additives. Alternatively, the reference electrode may be, for example, a thin film of Ag, which has been conditioned to form a Ag/AgCl reference electrode. In such a case, the reference fluid, for example, may be a 1.0 M KCl electrolyte.

In yet another example of the present invention, a sample probe is configured with an array of measurement microchannels and corresponding electrode sets so that more than one additive can be monitored concurrently. The measurement microchannels and electrode sets in the array may be of the type shown, for example, in FIG. 1, 5, 6, or 7. The measurement microchannels and corresponding electrode sets in the array may be fabricated on one or more discrete substrates. When the microchannels are fabricated on multiple discrete substrates, it may be advantageous to stack the substrates one upon the other to minimize sample probe dimensions or volume. Using a sample probe having several of the measurement microchannels to concurrently monitor a number of additives may greatly reduce the total time required for analyzing or determining plating bath composition. For example, a sample probe having six measurement microchannels may be used to concurrently monitor six additives in a plating bath. In such a case, the total time required for determining the bath composition may be reduced by a factor of six.

Electroless plating baths contain an even larger number of constituents than electroplating baths. A variety of these constituents may need to be monitored, and the present invention can be used as a method for determining bath composition, as discussed with reference to the exemplary systems shown in FIGS. 1, 5, 6, and 7. In an electroplating process, the current is typically controlled, and with knowledge of the surface area, principles based on Faradays' law can be used to relate the current utilized during the film growth process to determine the growth rate. In an electroless plating bath, there is no similar electrochemical measurement procedure that unambiguously provides the deposition rate. With the present invention, the flow of more than one specified fluid through a microfluidic channel can be easily controlled to provide a way of measuring the electroless plating deposition rate.

For this measurement, an electroless plating bath sample flows for a prescribed amount of time over a set of electrodes comprised of a metal or alloy upon which electroless plating readily occurs. Subsequently, a second fluid in which anodic stripping (i.e., dissolution) of the plated metal occurs at a reproducible current efficiency is pumped through the microchannel. Simultaneously, the working electrode in the electrode set is polarized to a potential at which the plated metal is oxidized or stripped by an external power supply or potentiostat. Measurement of the amount of current that passed just before the plated metal completely dissolves allows for the determination of the electroless plating rate by recording the current as a function of time while simultaneously controlling the flow rates through the microchannel. The prescribed amount of time during which the electroless deposition bath flows through the device is determined by the requirement that a sufficiently thick deposit is required to reduce uncertainty in the stripping analysis. This time may typically be in the range 1-10 minutes, but may require longer times if the electroless plating rate is very low. The stripping analysis will typically require less time.

Figure 8:
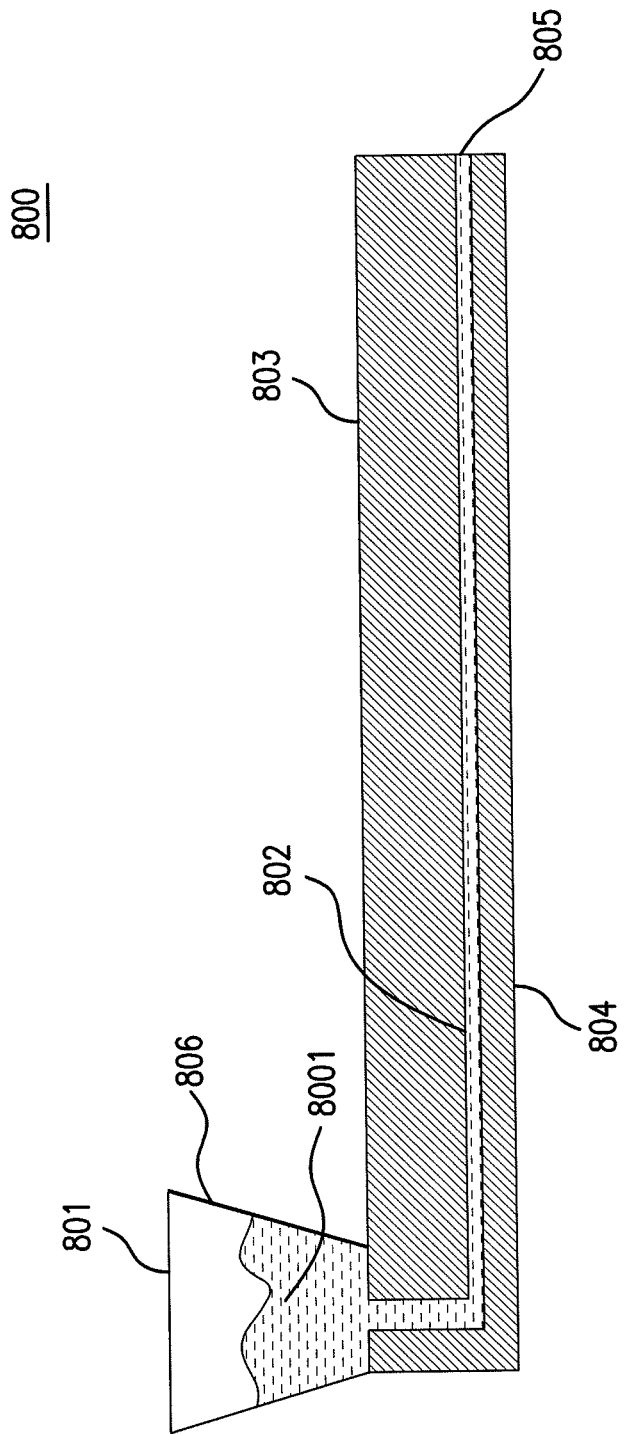
FIG. 8 is a schematic illustration of yet another microfluidic sampling device or probe for measuring the bath composition, in accordance with the principles of the present invention. The probe is configured so that flow through the microchannels is driven by a gravity feed tube.

The flow of the electroless plating bath sample and subsequently the stripping solution through the microchannels can be controlled by a large variety of different types of pumps. For example, syringe pumps have been used extensively in microfluidic studies. For some applications, a very low cost system may be desired. In such a case, flow can be controlled by the use of a gravity feed tube, for example, as shown in sample probe 800 (FIG. 8). Sample probe 800 includes a fluid input 801 into a gravity feed funnel 806. The level of input fluid 8001 builds up in the funnel 806. The difference in fluid level between the inlet and outlet of sample probe 800 forces the fluid to flow through microchannel 802 at an appreciable rate. The rate of flow in device 800 can be fixed or determined empirically by an operator. Furthermore, when the microchannel areal dimensions are very small compared to the dimensions of the gravity feed tube, the fluid level difference can be easily maintained constant, resulting in constant flow rates for the duration of the monitoring period.

In this embodiment, fluids can be switched manually utilizing, for example, a pipette to introduce and withdraw fluids from the gravity feed tube. Microchannel 802 may be constructed of PDMS 803, which is then placed onto a substrate 804. After the fluid flows through microchannel 802, the fluid leaves through fluid exit 805. The process of measuring plating rate is readily completed in less than 10 minutes, using less than 5 ml of input fluid and generating an equal amount of waste fluid that requires disposal.

While the above example involves electroless deposition processes, the present invention can be also applied to an electroplating process. This may be useful when the plating efficiency, i.e., the fraction of current that results in metal deposition, is not well known. For this embodiment, an electrodeposition bath sample flows for a prescribed amount of time over a set of electrodes comprised of a metal or alloy upon which electroplating readily occurs. Simultaneously, the working electrode in the electrode set is set to a potential at which the metal is deposited. Subsequently, a second fluid in which anodic stripping of the plated metal occurs at a reproducible current efficiency is pumped through the microchannel. Simultaneously, the working electrode in the electrode set is polarized to a potential at which the plated metal is oxidized or stripped by an external power supply or potentiostat. Measurement of the amount of stripping charge that passed just before the plated metal completely dissolves allows for the determination of the electrodeposition rate.

Figure 9:
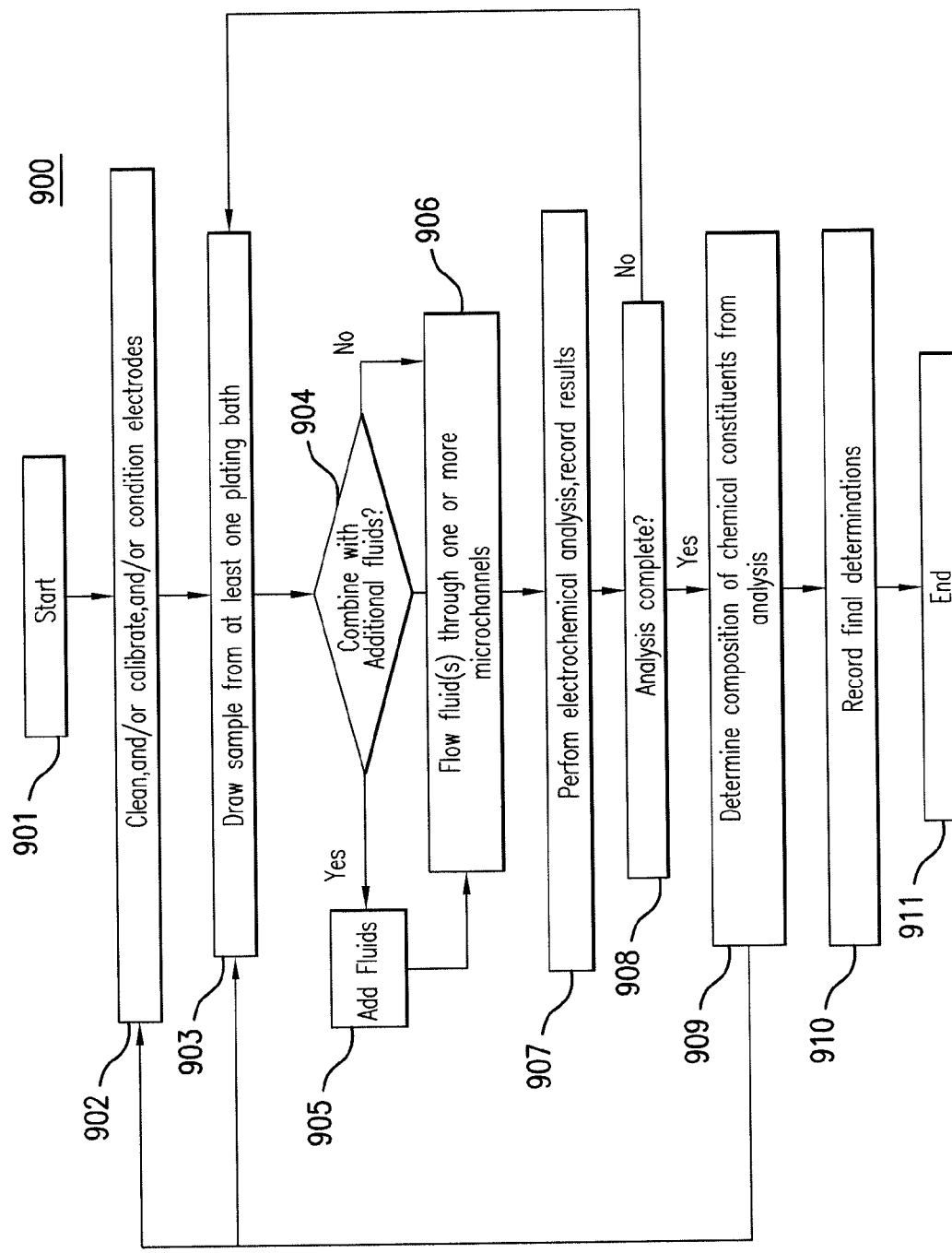
FIG. 9 is a flow diagram illustrating steps in an exemplary procedure for monitoring the composition of a copper plating bath in accordance with the principles of the present invention.

FIG. 9 shows a flow diagram of several steps in an exemplary procedure 900 for determining the amount of additives in a certain copper plating bath using the inventive monitoring systems and sampling probes (e.g., systems 100, 500, 600 or 700 shown in FIG. 1, 5, 6 or 7). Step 901 corresponds to a start or initiation of procedure 900. Next, at step 902, probe electrodes are calibrated, cleaned or conditioned to suitable specifications. After the electrodes are up to the desired specifications, at step 903 sample or test volumes of bath fluids are drawn. At steps 904 and/or 905, the drawn sample or test volumes may be mixed or combined with other chemical fluids or reagents in external pumping manifolds before insertion in the sample probe microchannels, or readied for unmixed insertion in the sample probe for later mixing in the microchannels. At step 906, the subject test fluids are inserted in the microchannels where they flow over the measurement electrodes in the sample probe. At step 907, as part of the electrochemical analysis, a specified current or potential may be applied to the electrodes to measure and record the electrochemical properties of the subject test fluids. At step 908, the performance of step 907 may be evaluated. Accordingly, step 907 and earlier steps 902-906 may be repeated if necessary or desired. At step 909, after successful performance of step 907, the measured data is processed to determine the concentration of additives in the subject test fluids. Steps 902 through 909 may be repeated as many times as desired or necessary for satisfactory characterization of the bath fluids. A repeat measurement may begin at either step 902 or at step 903, depending, for example, on electrode condition. Upon satisfactory characterization of the bath fluids, the results may be recorded at step 910 before procedure 900 is ended at step 911.

The microfluidic devices or sampling probes (e.g., devices 110, 510, 613, and 713) used in the monitoring systems may be designed to be consumable parts. Accordingly, the monitoring systems may be configured with suitable mechanical interfaces or connectors to facilitate quick and easy removal or replacement of the sample probes. Suitable mechanical interfaces are provided to interface sampling probes/substrates 110, 510, 613 or 713 to pump manifolds 7001-7003, 5001, 5002, 6001-6005, 1004 and the electrical wiring of suitable electronics 107, 610, 710, or 507. If desired the sampling probes may be treated as "one-time" use disposable parts. Such use may reduce monitoring process times, for example, by eliminating the time associated with the cleaning, conditioning, and calibration step 902 in monitoring procedure 900.

Figure 10:
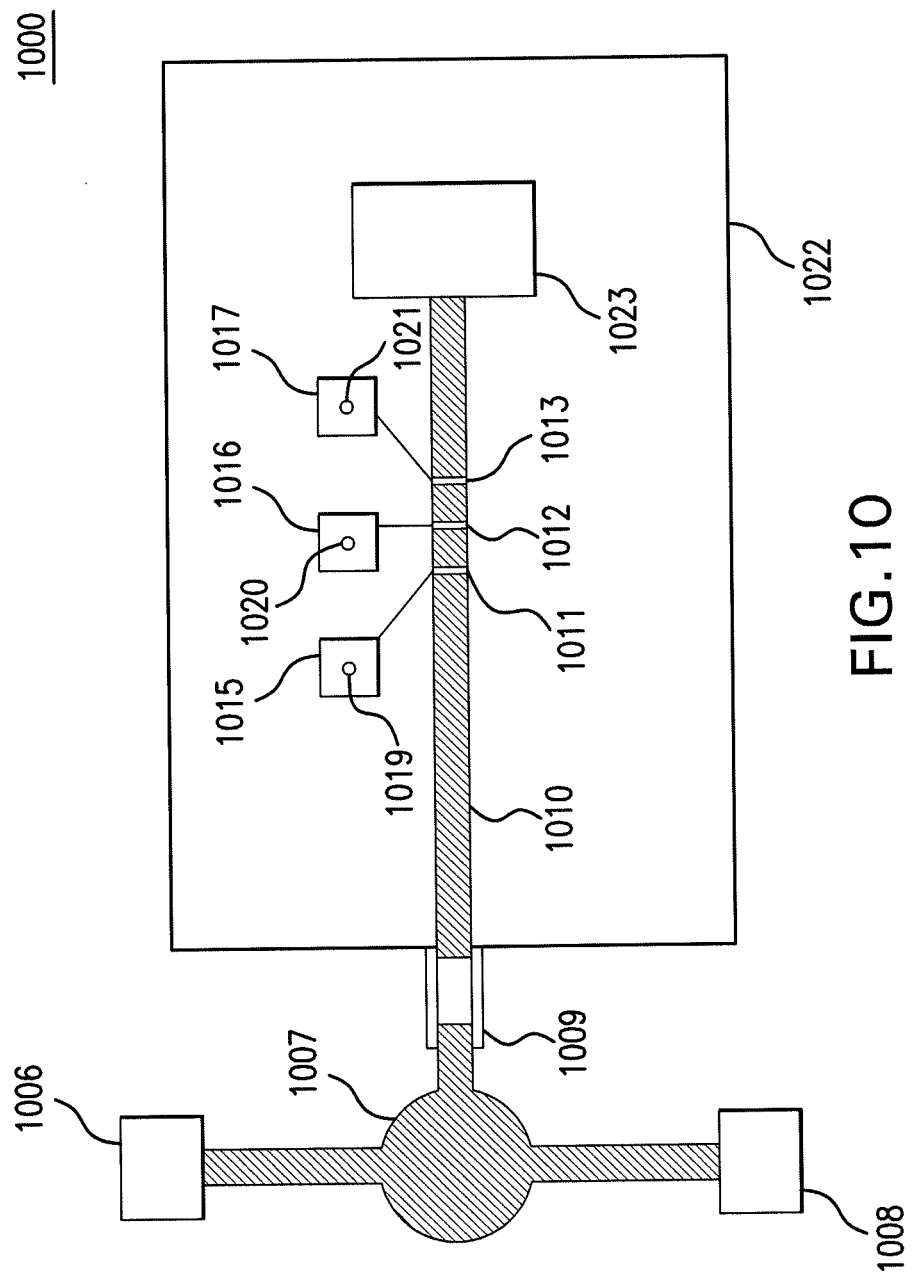
FIG. 10 is a schematic illustration of a simple mechanism for rapidly connecting and disconnecting a microchannel from the system electronics and manifold in accordance with the principles of the present invention.

FIG. 10 shows an exemplary interface configuration 1000, including electrical and mechanical connectors, which are suitable for rapidly connecting and disconnecting a microchannel 1010 on a sampling probe/substrate 1022 from an electrical potential source 107 (FIG. 1) and a pumping manifold 1007. In configuration 1000, pumps 1006 and 1008 remain connected to pumping manifold 1007. Substrate 1022 as shown has, for example, a waste fluid reservoir 1023 mounted on its surface. Reservoir 1023 is connected to microchannel 1010. In alternate versions of substrate 1022, mounting of waste fluid reservoir 1023 onto the substrate may be dispensed with to ensure a rapidly replaceable substrate. In such versions, a fluid reservoir may be provided off-chip with suitable provision of connecting tubing and an outlet port on the substrate.

Rapid exchanges of substrate 1022 are particularly useful when a sequence of varied measurements are desired without having to bear the time overhead of cleaning microchannel 1010 for each measurement. In order to rapidly exchange substrate 1022 in a monitoring set up, it may be desirable to disconnect manifold 1007 from microchannel 1010, which has internal electrodes 1011-1013. Manifold 1007 may be easily disconnected from microchannel 1010 by use of miniature, preferably flexible, connecting tubing 1009. Substrate 1022 is also provided with electrical connector parts designed for rapid electrical disconnection of the voltage source 107 from conducting pads 1015-1017, which lead to electrodes 1011-1013. For example, each of the pads 1015-1017 may be provided with a centrally located, tapped screw 1019-1021 which permit quick connection or disconnection of electrical wires from power supply or potentiostat 107.

Interface configuration 1000 permits the use of substrate 1022 together with its associated structures to be treated as a throwaway item, and thus makes it possible to obtain a rapid sequence of measurements by connecting a new sampling probe/substrate 1022 for each successive measurement. Suitable measurement protocols using throwaway microchannels may be designed to save cost and time.

The inventive microfluidic devices (e.g., devices 110, 510, 613, 713, 805, and 1010) also may be used as etch-rate monitors in etching processes. The use of such devices advantageously reduces the size of systems used for monitoring etching baths. In the present invention, microfluidic technologies are combined with electrochemical methods for monitoring etching baths.

The etching bath composition and the concentration of bath additives change with time. This may be significant especially after usage or longer periods of storage. Such conditions often require that baths used for an etching (or plating) process be checked or tested prior to further use. The systems and methods of the present invention can be used to monitor the effects due to storage or even the shipping time of the etchant from the manufacturer.

The systems and methods can also be used to monitor multiple additives or debris resulting from use of the etchant in an etching process. As mentioned above, etchants become ineffective after some time of usage since constituents in the etchant electrolyte can change. At the same time, the etched material may change the effectiveness or even poison the etchant. The microfluidic technique of the present invention can be used to effectively track the composition of the etchant in order to keep the etching process uniform and continuous, which is often the process requirement in commercial applications. With information provided by the microfluidic etching-bath monitors, users can choose, for example, to replenish additives or to replace a bath prior to introducing a valuable workpiece into an etching bath.

An exemplary application of the "microfluidic" systems and methods of the present invention is for monitoring the electrochemical-mechanical planarization (ECMP) process, which is an important process in the semiconductor industry. In this exemplary application, the etchant electrolyte, which may contain slurry, is monitored using the inventive microfluidic technique. The electrolyte properties may be monitored not only for the effectiveness of its etching capability, but also for the purpose of recycling the electrolyte that appears as runoff from the silicon wafer undergoing planarization. If it is found by the present microfluidic technique that the runoff is active as an etchant, it may be filtered for re-use, thereby presenting a substantial cost saving.

Another exemplary application relates to etching processes that are used to etch copper on semiconductor wafers for use in the computer industry. The economics of chip manufacturing demands a very high yield for each individual processing step. For etching steps, the yield can be greatly improved by maintaining electrolyte bath composition within a prescribed window of operation. However, presently available state-of-art etching rate monitors used in fabrication facilities are spatially large, require a significant amount of time to perform a complete bath analysis, and generate significant waste product per analysis. In some cases, etching bath monitors do not exist, and electrolyte is only used once, generating excessive waste.

An etch bath monitoring system of the present invention, which is based on the aforementioned microfluidic devices, uses electrochemical measurements to assess etchant properties. The electrochemical measurements require reproducible electrode surfaces and suitable electronics to allow for either two or three-electrode measurements in combination with an electrochemical cell. The suitable electronics can include a potentiostat, a galvanostat, or a power supply, which are combined with appropriate auxiliary equipment such as multimeters, voltmeters, coulometers, etc. A means of recording the electrochemical measurements is also required. Typically, recording of the electrochemical measurements may be achieved by interfacing a computer to the electronics. In a low-cost embodiment of the present invention, the recording device may be an analog readout of the measurements obtained by the suitable electronics.

Conventional electrochemical measurements require a reproducible and controllable fluid flow within the electrochemical cell. A facile method of creating reproducible flow conditions using, for example, a rotating disk electrode, is well known to those skilled in the art. The disadvantage of a rotating disk electrode is its associated requirement of a relatively large volume of fluid in the electrochemical cell. This large volume of fluid is associated with a correspondingly large amount of waste, since the fluid can generally not be re-used.

Further, the results of an electrochemical measurement generally depend on all chemical additives or constituents that affect the electrochemical response of the measurement system. Therefore, in practice, for monitoring etch baths, the electrochemical measurements are conventionally performed periodically not only on an etchant bath sample but on combinations of the etchant bath sample with one or more additional fluids (e.g., a second fluid, a third fluid, etc.) that are designed to isolate the effects of each additive or constituent. By repeating and recording the electrochemical measurement on a series of combinations of etchant bath samples and different additional fluids, the concentration of each additive or constituent in a bath may be determined. In conventional bath monitoring systems, the electrochemical measurements on a series of combinations not only generates excessive waste but also is time consuming—measurement times of the order of an hour are typically required for a complete analysis. Furthermore, because of the volume requirements of the various fluids, an etchant bath monitor system using a conventional rotating disk electrode is large and disadvantageously occupies very valuable real estate in a fabrication facility.

In contrast to the conventional monitor systems, the present invention, utilizing microfluidic technologies, provides etchant bath monitor systems that are compact and suitable for quick yet complete characterization of the etchants. Further, the microfluidic devices used in the inventive etchant bath monitor systems allow for reproducible and controllable fluid flows near the electrode surfaces using only minimal amounts of the fluids.

The operation of a "microfluidic device" etchant bath monitoring system may be understood with reference to its use for monitoring a copper etchant bath. In the monitoring procedure, first a copper composition is deposited on an inert electrode (e.g., platinum electrode) in the microfluidic device. Then, the etchant is introduced into the microfluidic device to etch the deposited copper. Further, a second fluid may be mixed with the introduced etchant to etch the deposited copper. The stripping current characteristics, which are measured during the etching of the deposited copper layer, provide quantifiable information on the etch rate, bath etchant composition and constituents. With knowledge of the surface area, one skilled in the art can use principles based on Faradays' law to relate the current utilized during the etching of the copper deposition removal process to determine the etch rate in units for example of micrometers per minute.

An exemplary microfluidic etching bath monitor device may be device 110, which was described above with reference to FIG. 1. As noted earlier, electrodes 104, 105, and 106 in device 110 may be fabricated from a variety of suitable materials. For example, the working electrode 105 and counter electrode 106 may be made of Pt, as Pt is well known to be an ideal electrode due to its inertness and stability in many electroplating and etching baths. The reference electrode 104 may be a thin film of Pt upon which a second thin film of copper is deposited prior to the monitoring operation. Other materials may be more appropriate when monitoring etchants other than copper etching baths. It will be noted that the present invention is not limited to the use of Pt as an electrode or part of an electrode structure.

With renewed reference to FIG. 1, test solutions 1001 (fluid 1) and 1002 (fluid 2) comprising the etching bath sample and a second fluid, respectively, are mixed off substrate 110 in a manifold 1003 by using pumps 101 and 102, respectively. Manifold 1003 leads to the microchannel 103. The mixed fluids (i.e., a test solution 1004) flow through the microchannel 103 for measurement. Suitable electronics such as potentiostat 107 are used for electrochemical measurements, which characterize the test solution while the fluid flows continuously through the microchannel 103. When the first electrochemical measurement is completed and results are recorded through the use of computer 108, an additional or mixing of two additional fluids 1 and 2 in manifold 1003 will generate second test solution 1004. This procedure of mixing fluids 1 and 2 can be repeated by mixing different sets of etching bath samples containing different compositions of additives in manifold 1003 using pumps 102 and 101. Each etching bath sample provides a different test solution 1004. This procedure may be repeated several times until the bath is characterized as thoroughly as desired by the user. After flowing through microchannel 103, test solution 1004 is expelled from microchannel 103 into a fluid disposal chamber 109.

As part of the etchant characterization method, cleaning fluids, conditioning fluids or other fluids such as fluids intended to calibrate the electrodes, may be inserted into microchannel 103. The cleaning, conditioning, or calibration processes may be performed at the same time as electrochemical processing. The insertion of such fluids may occur prior to testing, after testing, and between insertions of different test solutions 1004.

The operation of device 110 was described above with reference to FIGS. 2-4, which show plating bath monitoring data. It is readily understood that the data also illustrates how the present invention is used to monitor an etchant bath in an analogous manner. However, for brevity, the description of FIGS. 2-4 is not repeated herein.

It will be understood that the etchant bath monitoring systems may employ microfluidic devices other than device 110. The etchant bath monitoring systems may, for example, use any of devices 510, 613, 713, 805, and 1010, which have been previously described with reference to FIGS. 5, 6, 7, 8, and 10, respectively.

The foregoing merely illustrates the principles of the invention. Various modifications and alterations to the described embodiments will be apparent to those skilled in the art in view of the teachings herein. It will be appreciated that those skilled in the art will be able to devise numerous modifications which, although not explicitly described herein, embody the principles of the invention and are thus within the spirit and scope of the invention.

The invention claimed is:

1. A microfluidic system for monitoring the composition of electrolyte bath fluids, the microfluidic system comprising:
   (a) a sampling probe comprising:
      (i) a chip substrate having a measurement microchannel wherein the measurement microchannel has areal dimensions of less than 0.006 sq. mm; and
      (ii) a set of electrodes disposed on an inner surface of the measurement microchannel;

(b) monitoring electronics connected to the set of electrodes, wherein the monitoring electronics and set of electrodes are configured to measure one or more electrochemical properties of a predetermined volume of the bath fluids pumped through the measurement microchannel of the microfluidic system; and an external fluid pumping arrangement connectable to an inlet disposed at an end of the measurement microchannel.

2. The system of claim 1 wherein electrolyte bath fluid comprises one of a plating solution and an etching solution.

3. The system of claim 1 wherein the electrodes are thin film metallic electrodes.

4. The system of claim 1 wherein the external fluid pumping arrangement comprises a mixing manifold, whereby samples of bath fluids and other fluids can be mixed prior to insertion in the measurement microchannel.

5. The system of claim 1 wherein the chip substrate further comprises a micro mixing manifold connected to the measurement microchannel, whereby samples of bath fluids and other fluids can be mixed prior to insertion in the measurement microchannel.

6. The system of claim 1 wherein the chip substrate further comprises a waste reservoir disposed at an end of the microchannel.

7. The system of claim 1 further comprising a waste reservoir, which is disposed external to the chip substrate and adapted for connection to an end of the microchannel.

8. The system of claim 1 wherein
the chip substrate comprises an array of microchannels including at least one measurement microchannel, each microchannel adapted for connection to the external fluid pumping arrangement.

9. The system of claim 8 wherein the array of microchannels comprises a pair of microchannels in fluid communication with the measurement microchannel, whereby the microfluidic system is configured such that a pair of fluids inserted in the pair of microchannels are mixed prior to flow through the measurement microchannel.

10. The system of claim 8 wherein the array of microchannels comprises a set of a number of microchannels in fluid communication with the measurement microchannel, whereby any combination of a corresponding number of fluids can be inserted in the measurement microchannel.

11. The system of claim 8 comprising a plurality of measurement microchannels.

12. A microfluidic system for determining additive concentrations in an etching bath solution, the microfluidic system comprising:
a) a chip substrate having at least one microchannel and a set of thin film electrodes disposed on an interior surface of the microchannel wherein the at least one microchannel has areal dimensions of less than 0.006 sq. mm;
b) at least one pump connected to the microchannel for flowing fluids through the microchannel;
c) at least one of a potentiostat and a power supply that are electrically connected to the electrodes; and
d) means for measuring an electric current when a voltage is applied to said electrodes, wherein the electric current is function of the composition of fluids flowing through the microchannel of the microfluidic system.

13. The system of claim 12 further comprising means for controlling the temperature of the substrate and the microchannel.

14. The system of claim 12 wherein the fluids flowing through the microchannel comprises one of an etching bath sample, a second fluid, a plating fluid, a reference fluid, an electrode cleaning fluid, an electrode conditioning fluid, a calibration fluid, and any combination thereof.

15. The system of claim 12 wherein the thin film electrodes comprises at least one of a working electrode, a reference electrode and a counter electrode.

16. A method of monitoring the composition of plating or etching bath fluids, the method comprising:
(a) providing a microfluidic sampling probe that comprises:
a chip substrate having a measurement microchannel;
a set of electrodes disposed on an inner surface of the measurement microchannel wherein the measurement microchannel has areal dimensions of less than 0.006 sq. mm; and
an external fluid pumping arrangement connectable to an inlet disposed at an end of the measurement microchannel;
(b) flowing a test sample of the bath fluids through the measurement channel; and
(c) applying and measuring electrical voltages and/or currents at the electrodes to determine one or more electrochemical properties of the test sample of the bath fluids flowing through the measurement microchannel, wherein the determined electrochemical properties correspond to a composition of the bath fluids.

17. The method of claim 16, wherein the test sample of the bath fluids comprises a mixture of the bath fluids and another testing fluid.

18. The method of claim 16, wherein the sampling probe comprises a number of microchannels in fluid communication with the measurement microchannel, and wherein differently prepared test samples are sequentially drawn through the number of microchannels and inserted in the measurement microchannel to determine one or more electrochemical properties of the test sample of the bath fluids flowing through the measurement microchannel.

19. The method of claim 16, wherein the sampling probe comprises an additional measurement channel having disposed therein a reference electrode, wherein flowing a test sample of the bath fluids through the measurement channel further comprises flowing a reference fluid through the additional measurement channel.

20. A method of monitoring an etching bath, the method comprising:
providing a microchannel having areal dimensions of less than 0.006 sq. mm;
controlling a flow rate of a test solution of the etching bath through a microfluidic sampling probe comprising a chip substrate having a microchannel having a working electrode comprising an etchable material and a reference electrode disposed in the microchannel;
applying a voltage between the working and reference electrodes;
measuring and recording the current flowing between the working and counter electrodes; and
measuring the dissolution of the etchable material from the working electrode.

21. The method of claim 20 further comprising heating the test solution flowing through the microchannel.

* * * * *